(12) United States Patent
Bodenschatz et al.

(10) Patent No.: US 7,115,106 B2
(45) Date of Patent: Oct. 3, 2006

(54) BANDAGE FOR THE ANKLE JOINT

(75) Inventors: Stefan Bodenschatz, Buxtehude (DE); Arthur Hugh Andrews, Kölln-Reisiek (DE)

(73) Assignee: Beiersdorf AG, Hamburg (DE)

( * ) Notice: Subject to any disclaimer, the term of this patent is extended or adjusted under 35 U.S.C. 154(b) by 20 days.

(21) Appl. No.: 10/275,261

(22) PCT Filed: Apr. 4, 2001

(86) PCT No.: PCT/EP01/03797

§ 371 (c)(1),
(2), (4) Date: Mar. 12, 2003

(87) PCT Pub. No.: WO01/85078

PCT Pub. Date: Nov. 15, 2001

(65) Prior Publication Data

US 2003/0171707 A1    Sep. 11, 2003

(30) Foreign Application Priority Data

May 9, 2000    (DE) ................................ 100 22 524

(51) Int. Cl.
*A61F 5/00*    (2006.01)

(52) U.S. Cl. ........................................................ 602/65

(58) Field of Classification Search ............ 602/60–63, 602/65, 1, 27, 23, 5; 128/869, 882, 892, 128/893, 894

See application file for complete search history.

(56) References Cited

U.S. PATENT DOCUMENTS

| | | | | | |
|---|---|---|---|---|---|
| 2,484,130 | A | * | 10/1949 | Thibault | 602/62 |
| 3,312,219 | A | * | 4/1967 | Peckham | 602/65 |
| 3,490,450 | A | * | 1/1970 | Gardner | 602/65 |
| 3,506,000 | A | * | 4/1970 | Baker | 602/65 |
| 3,508,544 | A | * | 4/1970 | Moore et al. | 128/892 |
| 3,515,136 | A | * | 6/1970 | Baker | 602/65 |
| 3,699,959 | A | | 10/1972 | Garrahan et al. | |

(Continued)

FOREIGN PATENT DOCUMENTS

DE    3122463    12/1982

(Continued)

OTHER PUBLICATIONS

English Language Abstract for DE Appln. No. 43 18 791.

(Continued)

*Primary Examiner*—Michael A. Brown
*Assistant Examiner*—Huong Q. Pham
(74) *Attorney, Agent, or Firm*—Greenblum & Bernstein, P.L.C.

(57) ABSTRACT

Bandage for an ankle joint comprising an elongated tape, wherein the elongated tape runs around a heel, across a lateral side of the ankle joint, across an instep in a medial plantar direction and across a sole of a foot in a lateral plantar direction. First and a second transverse edges of the elongated tape are fastened to the tape itself. A first bridle and a second bridle is attached to the elongated tape. The first bridle extends from a lateral side on a forefoot and the second bridle extends from a lateral side on the ankle joint. The second bridle is circularly closed around the ankle joint and extends to the lateral side of the ankle joint. The first bridle is guided on the forefoot across the instep to the ankle joint and is circularly closed around the ankle joint and over the second bridle. The first bridle extends to the lateral side of the ankle joint. This Abstract is not intended to define the invention disclosed in the specification, nor intended to limit the scope of the invention in any way.

29 Claims, 1 Drawing Sheet

U.S. PATENT DOCUMENTS

| | | | |
|---|---|---|---|
| 3,777,751 A | | 12/1973 | Wise |
| 3,989,041 A | * | 11/1976 | Davies .................. 602/62 |
| 4,345,590 A | * | 8/1982 | Nakajima ................ 602/65 |
| 4,367,733 A | | 1/1983 | Stromgren |
| 4,401,113 A | * | 8/1983 | Incorvaia ............... 602/65 |
| 4,590,932 A | * | 5/1986 | Wilkerson .............. 602/65 |
| 4,597,395 A | | 7/1986 | Barlow et al. |
| 4,630,600 A | * | 12/1986 | Spencer et al. ......... 602/27 |
| 4,729,370 A | | 3/1988 | Kallassy |
| 4,984,566 A | * | 1/1991 | Sekine et al. ............ 602/6 |
| 5,038,762 A | | 8/1991 | Hess et al. |
| 5,090,404 A | | 2/1992 | Kallassy |
| 5,139,479 A | | 8/1992 | Peters |
| 5,385,036 A | * | 1/1995 | Spillane et al. ......... 66/87 |
| 5,403,267 A | * | 4/1995 | Pearce et al. ............ 602/8 |
| 5,472,411 A | | 12/1995 | Montag et al. |
| 5,480,708 A | * | 1/1996 | Cheng .................. 442/306 |
| 5,505,692 A | * | 4/1996 | Cho ........................ 602/8 |
| 5,620,413 A | * | 4/1997 | Olson ..................... 602/65 |
| 5,833,640 A | * | 11/1998 | Vazquez et al. ........ 602/27 |
| 5,843,010 A | * | 12/1998 | Bodmer ................. 602/27 |
| 5,891,073 A | * | 4/1999 | Deirmendjian et al. ... 602/27 |
| 5,897,518 A | * | 4/1999 | Shaw ..................... 602/65 |
| 5,918,602 A | * | 7/1999 | Shaw et al. ............ 128/882 |
| 6,024,712 A | * | 2/2000 | Iglesias et al. .......... 602/6 |
| 6,083,185 A | * | 7/2000 | Lamont ................. 602/65 |
| 6,126,625 A | * | 10/2000 | Lundberg .............. 602/27 |
| 6,196,986 B1 | * | 3/2001 | Gardiner ............... 602/63 |
| 6,322,530 B1 | * | 11/2001 | Johnson et al. ........ 602/65 |
| 6,406,450 B1 | * | 6/2002 | Kowalczyk et al. .... 602/27 |
| 6,555,730 B1 | * | 4/2003 | Albrod et al. .......... 602/58 |
| 6,582,382 B1 | * | 6/2003 | Domanski et al. ...... 602/1 |
| 2001/0014783 A1 | | 8/2001 | Bodenschatz et al. |

FOREIGN PATENT DOCUMENTS

| | | |
|---|---|---|
| DE | 3415657 | 10/1985 |
| DE | 3416253 | 11/1985 |
| DE | 3909922 | 2/1990 |
| DE | 3840714 | 6/1990 |
| DE | 9211750 | 4/1993 |
| DE | 4318588 | 8/1994 |
| DE | 4318791 | 12/1994 |
| DE | 19802511 | 8/1999 |
| WO | 9219187 | 11/1992 |

OTHER PUBLICATIONS

English Language Abstract for DE Appln. No. 34 16 253.
English Language Abstract for DE Appln. No. 39 09 922.
English Language Abstract for DE Appln. No. 34 15 657.
English Language Abstract for DE Appln. No. 31 22 463.

* cited by examiner

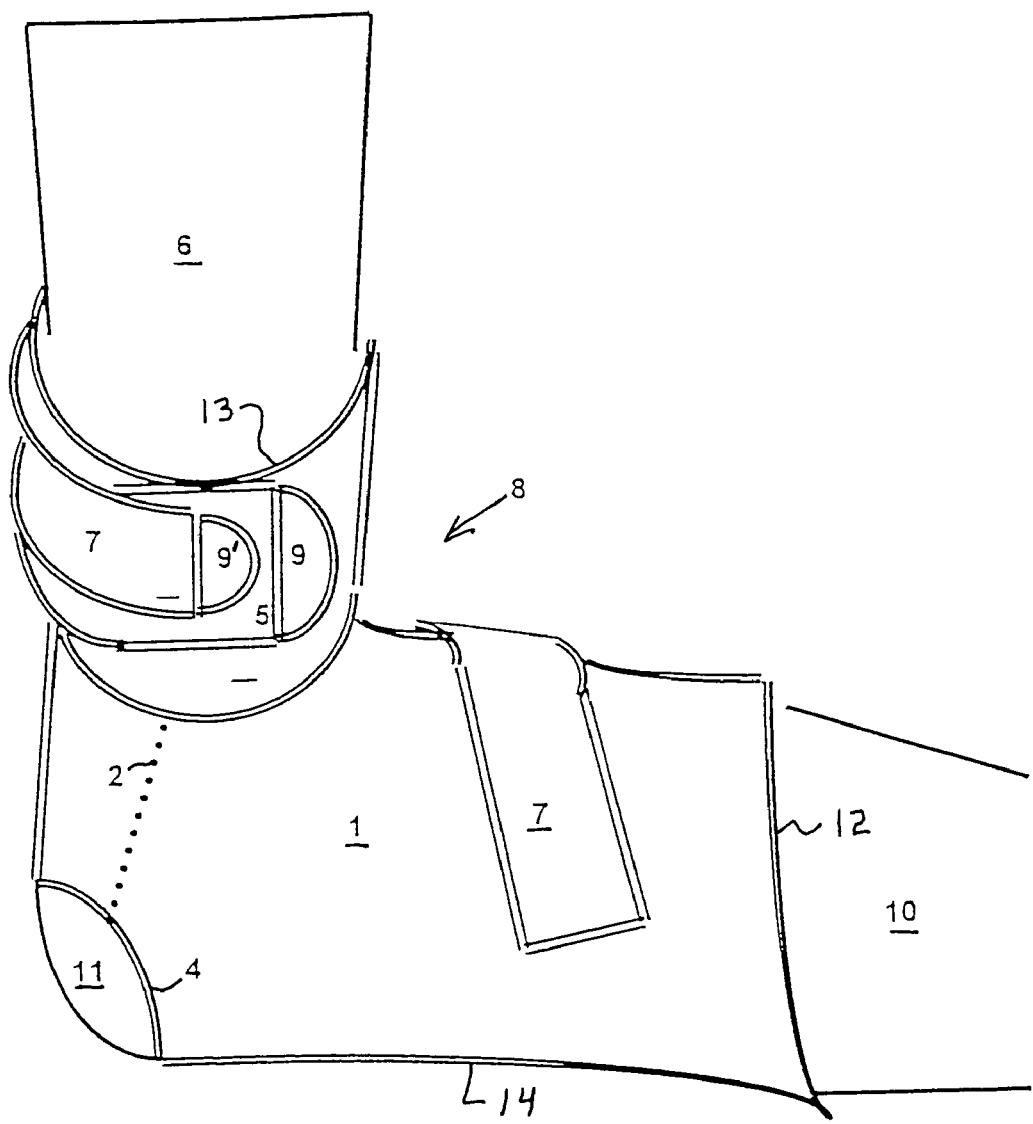

BANDAGE FOR THE ANKLE JOINT

CROSS-REFERENCE TO RELATED APPLICATIONS

The present application is a U.S. National Stage of International Application No. PCT/EP01/03797, filed Apr. 4, 2001, which claims priority under 35 U.S.C. § 119 of German Patent Application No. 100 22 524.1, filed May 9, 2000.

BACKGROUND OF THE INVENTION

1. Field of the Invention

The invention relates to a bandage for the ankle joint.

2. Discussion of Background Information

Depending on their design and range of indications orthopaedic bandages carry out a fixing, guiding, bracing and/or supporting function on the limbs of the human body. The form of these medical bandages must be such as to correspond to the anatomical circumstances in order to exert an influence from outside on the human body by means of form and force-fit The manufacture of such medical bandages is effected by cutting to size blanks made of sheet materials such as neoprene, knits or fabrics. The anatomical form is achieved by the shaping of the blanks or darts, for example with gussets, and the subsequent joining of the blanks as in the case of clothing.

Joining can be effected by means of sewing, bonding or other standard procedures. The major disadvantages of such bandages are that it is difficult to achieve an exact anatomical fit and that a large number of joins thereby result, for example seams. These joins affect the characteristics of the material used, and there is the risk of pressure sores on the skin.

Ankle joint orthotic devices or bandages are primarily used for the early functional treatment of fresh fibular ligament ruptures and minor and moderately severe tarsal distortions as well as for chronic instability.

DE 38 40 714 A1 reports of an ankle joint orthotic device with a U-shaped support, whose sidepieces come together in a bridge under the foot, reach over the ankle and which are held together at the ends by a fixing strap. Here the outer sidepiece extends upwards at the side before the ankle and the inner sidepiece opposite the outer sidepiece before the Achilles tendon. Both sidepieces run towards the bridge to a position before the heel and continue upwards towards their ends in such a manner that they extend upwards laterally next to the edges of the shinbone more or less parallel to same, including a retaining band at the bottom of the sidepieces, which runs diagonally upwards from the one sidepiece across the instep to the other sidepiece with means of attachment, is guided around the Achilles tendon above the ankle and ends in a retention piece on the instep crossing over at the other sidepiece. This design of ankle joint orthotic device is supposed to prevent sprains, in particular in a lateral/forward direction, i.e. towards an equinus position. As the U-shaped support of this ankle joint orthotic device extends upwards laterally with its outer sidepiece before the malleolus and with its inner sidepiece before the Achilles tendon and is held together by a bridge running underneath the foot, the medial edge of the metatarsus is not included, thus limiting the use of this ankle joint orthotic device.

A foot fixing splint is described in DE 39 09 922 A1. In particular, this foot fixing splint is used for the post-operative treatment of an injured ankle joint, with a foot-piece encompassing the foot, which is attached to a retention piece extending upwards to the calf equipped with closing pieces. The retention piece is divided into two side-sections, which are joined to the foot-piece and are dish-shaped. Each part of the side-section covering the malleolus is provided with a cut-out in the form of a window. The area of the Achilles tendon on the foot-piece and the retention piece is thus cut away. The adjustable and fixable band-shaped closing pieces are made of non-elastic material, with one closing piece being positioned on the foot-piece so it secures the instep from supinatory rising overlapping the first ray of the metatarsus. The objectives of such a foot fixing splint are firstly to achieve absolute immobilization of the foot to be treated and secondly, to avoid the disadvantages of a plaster cast: after injuries and operations on the outer ligaments the foot is frequently put in plaster to immobilize it, thus precluding any postoperative treatment of surgical wounds due to numerous major disadvantages. This foot fixing splint is based on a U-shaped joint sleeve with a section covering the entire sole of the foot, encompassing the metatarsus and forefoot to the ball of the little toe, without however sufficient flexibility being provided in the metatarsal area.

DE 43 18 588 C2 also reports of an ankle joint orthotic device consisting of a U-shaped joint sleeve made of thermoplastic material, which includes a lateral malleolus splint and an inner malleolus splint. These ankle splints are joined together by a bridge passing under the heel. The ankle splints also include anatomically shaped depressions catering for the contours of the ankle and ensuring an anatomical fit. Another element of the orthotic device is its metatarsal section, which is likewise made of thermoplastic material. This part of the orthotic device passes crosswise under the sole of the foot proximally to the capituia of the metatarsalia I–V and is designed medially and laterally in the form of a tab. These shaped tabs encompass the edges of the foot at the outside and inside. They firstly guide the metatarsus and secondly, are used to fix transverse and cross strips in place. The metatarsal section is connected at the sole of the foot by a bridge also made of thermoplastic material which is nevertheless highly flexible. This bridge has the function of a joint and operates in the manner of a hinge consisting of a film material. The rotational axis of this joint designed as a highly flexible bridge runs dorsomedially in an anterolateral direction and forms an angle of approx. 10° with the longitudinal axis of the foot, according to the anatomy of the lower ankle joint.

DE 34 15 657 C2 relates to an ankle bandage with an angled, tube-shaped ankle sock. A drawstrap is attached to the ankle sock. The ankle sock consists of a closed body with an opening only for the end of the foot and the leg. A sock is comparatively complicated and expensive to manufacture. It also has practical disadvantages as it may result in an accumulation of heat at the foot among other things, particularly when made of the rubber fabric generally used. An accumulation of heat then results in an unpleasant increase in sweating.

DE 31 22 463 C2 describes a bandage for the ankle joint which must include the additional features of two attachment strips with Velcro closures on both sides and two fixing and bracing strips to ensure proper positioning on the foot as well as adequate stabilization of the joint.

DE 43 18 791 C2 reports of an ankle joint bandage whose design can be described as complex. This ankle joint bandage consists of a lower-leg section and a foot section to which a pronation band is attached The lower-leg section includes two tabs which can be made to partially overlap, forming a tube encompassing the lower leg by means of a fast closure.

DE 92 11 750 U 1 describes an ankle joint bandage which offers very little relevance in practical terms as it only surrounds the upper part of the ankle joint and invariably requires a mobile connection to a shoe to be worn, which is created by means of straps The ankle joint bandage reported in WO 92/19187 A1 consists of a sock sewn from a blank to which a band is attached. In addition, the band starts at the ankle joint when the bandage is in place, and not at the sole of the foot, in the case of the bandage forming the subject of the invention.

U.S. Pat. No. 3,699,959 A shows a bandage consisting of two strips, with the shorter being firmly sewn to the longer in such a manner as to encompass the foot at the heel. The longer of the two strips is then wound round the foot in the shape of a cross in a complicated movement.

U.S. Pat. No. 3,777,751 A shows a bandage for the ankle joint that likewise consists of two bands. The first of the two bands is sewn to itself to form a closed circle. The second band is also attached by being directly stitched in place at this point. Several strips of adhesive tape encompassing the leg are used to finally attach the second band to same.

DE 198 02 511 A1 reports of a bandage which is suitable for functional treatment of minor and moderately severe tarsal distorsions and chronic instability in the case of the ankle joint. The bandage consists of a longitudinal strip and a band attached to the longitudinal strip. The first transverse edge of the strip is basically positioned vertically on the medial side of the ankle joint. Starting from the first transverse edge the longitudinal strip is wound around the heel, across the lateral side of the ankle joint, across the instep in a medial plantar direction and across the sole of the foot in a lateral plantar direction. The first transverse edge of the longitudinal strip is attached to the longitudinal strip itself, preferably by means of stitching. In addition, the second transverse edge is the starting point for the band which is guided from the lateral side of the sole of the foot across the instep to the medial side of the ankle joint, around the heel to the lateral side of the ankle joint and across the lateral side of the ankle joint and fixed in place.

SUMMARY OF THE INVENTION

The invention is based on the problem of creating a bandage which can be used for the ankle joint in particular and as such is suitable for functional treatment of minor and moderately severe tarsal distorsions and chronic instability and provides for specific lateral and medial stabilisation of the upper and lower ankle joint, with the risk of both inversion and eversion trauma being reduced and offering particularly simple and reliable usage for the patient.

The invention therefore provide for a bandage for an ankle joint comprising an elongated tape, wherein the elongated tape runs around a heel, across a lateral side of the ankle joint, across an instep in a medial plantar direction and across a sole of a foot in a lateral plantar direction, wherein a first and a second transverse edge of the elongated tape are fastened to the tape itself, wherein a first bridle and a second bridle are attached to the elongated tape, the first bridle extending from a lateral side on a forefoot and the second bridle extending from a lateral side on the ankle joint, wherein the second bridle is circularly closed around the ankle joint and extends to the lateral side of the ankle joint and the first bridle is guided on the forefoot across the instep to the ankle joint and is circularly closed around the ankle joint and over the second bridle, and wherein the first bridle extends to the lateral side of the ankle joint.

The present invention also provides a bandage for an ankle joint which comprises an elongated tape that runs around the heel, across the lateral side of the ankle joint, across the instep in a medial plantar direction and across the sole of the foot in a lateral plantar direction. The transverse edges of the elongated tape are fastened to the tape itself, and two bridles are attached to the elongated tape, one bridle extending from the lateral side on the forefoot and the other bridle extending from the lateral side on the ankle joint. The latter bridle is circularly closed around the ankle joint and the former bridle is guided on the forefoot across the instep to the medial side of the ankle joint and is circularly closed around the ankle joint.

In one aspect, the material of the elongated tape preferably has a lengthwise elasticity of from 60% to 250%, e.g., from 80% to 140%. In another aspect, this material preferably has a crosswise elasticity of up to 100%, e.g., of from 5% to 30%.

In yet another aspect, the material of the two bridles preferably has a lengthwise elasticity of up to 250%, e.g., from 30% to 100%. In a still further aspect, this material preferably has a crosswise elasticity of up to 100%, e.g., of from 5% to 30%.

In another aspect, the material of the elongated tape may comprise a textile strip and/or a neoprene foam. Preferably, the material comprises a spacer fabric.

In yet another aspect, the material of the two bridles may comprise a textile strip and/or a neoprene foam. Furthermore, the bridles may have a velcro strip attached at the ends thereof. In another aspect, the bridles of the bandage of the present invention may be individually adjustable.

In another aspect, the bandage may be capable of being changed over from the right ankle joint version or the left ankle joint version to a version for the respective opposite ankle joint by a rotation of the bandage by 180 degrees.

The present invention also provides a method of treating tarsal distortion and chronic instability of an ankle joint. This method comprises the stabilization of the ankle joint with the bandage of the present invention as set forth above.

The invention also relates to a bandage for the ankle joint, comprising an elongated tape, whereby the elongated tape runs around the heel, across the lateral side of the ankle joint, across the instep in a medial plantar direction and across the sole of the foot in a lateral plantar direction, whereby the first and second transverse edge of the tape are fastened to the tape itself. Two bridles are attached to the elongated tape, the first extending from the lateral side on the forefoot and the second from the lateral side on the ankle joint, with the second bridle being circularly closed around the ankle joint and the first bridle being guided on the forefoot across the instep to the medial side of the ankle joint and then circularly closed around the ankle joint.

The elongated elastic tape thus results in a closed figure of eight.

The material for the elongated tape preferably offers a lengthwise elasticity of 60% to 250%, in particular 80% to 140%, and a crosswise elasticity of up to 100%, in particular 5% to 30%.

The bridles can be made of elastic attachable textile strips, but also of neoprene foam for example. In a further advantageous version of the bandage the material of the bridles offers a lengthwise elasticity of up to 250%, in particular 30% to 100%, and a crosswise elasticity of up to 100%, in particular 5% to 30%.

Enveloping the foot in elastic tape results in a compressive effect. The form of the elastic tape, a figure of eight, corresponds to the anatomical circumstances. The circular bridle at the top of the bandage provides for individual adjustment of the compressive effect and thus individual lateral and medial stabilisation of the upper and lower ankle joint.

The individually adjustable lateral bridle, running from the forefoot and over the instep to the ankle joint, reduces the risk of both inversion and eversion trauma by way of lateral and medial stabilisation.

As both bridles are individually adjustable, it is possible to adjust the level of compression and support accordingly depending on the indication. Despite good stabilisation the bandage provides for the physiological gait pattern.

The bandage can be used for either the right or left foot The bandage should be fitted so that the bridles are positioned laterally.

The bandage is donned as for a sock. The circular strap is then closed first, followed by the lateral strap. This means that the bandage is simple to put on for the patient. Thanks to the opening in the heel section there is no problem in placing the bandage securely on the foot in the correct position.

The bridles of the bandage are provided with Velcro closures but can also be closed with press fasteners etc.

A material that does not irritate the skin is used as the material for the bandage. This means that textile strips can be utilized, but also neoprene foam for example. Spacer fabric, which is highly breathable, can be used to particular benefit.

BRIEF DESCRIPTION OF THE DRAWINGS

The sole FIGURE illustrates a bandage installed on the foot of a user.

DETAILED DESCRIPTION OF THE INVENTION

The invention is explained in greater detail by means of a diagram of an example of the design, namely positioned on the right foot 10. The version of the bandage for the left foot is designed as a mirror-image of the first. In the preferred version it can be changed over from the right to the left version by reversing the bandage.

The elastic tape 1 is attached to itself with the two fronts 2 (only one of which is shown) to form a sock 3 which has the figure of an eight. The sock 3 has foot opening 12 for the foot, a leg opening 13, and a heel opening 4. The bandage is placed on the foot 10 so that the bridles or strips 5, 7 are in a lateral position and the heel 11 is exposed in the heel opening 4. The upper bridle or strip 5 is then closed circularly on itself around the ankle joint 6 using the attached first Velcro strip 9. The lateral lower bridle 7 is guided over the instep 8 and also closed circularly on itself around the ankle joint 6 using the attached second Velcro strip 9'.

The bandage for an ankle joint thus formed by an elongated tape 1 that runs around the heel 11, across the lateral side of the ankle joint 6, across the instep 8 in a medial plantar direction and across the sole 14 of the foot 10 in a lateral plantar direction. The transverse edges of the elongated tape are fastened to the tape itself at locations 2, The two bridles 5 and 7 are attached to the elongated tape 1. One bridle 7 extends from the lateral side on the forefoot and the other bridle 5 extends from the lateral side on the ankle joint 6. The upper bridle 5 is circularly closed around the ankle joint 6 and the lower bridle 7 is guided on the forefoot across the instep 8 to the ankle joint 6 and is circularly closed around the ankle joint 6.

The material of the elongated tape 1 preferably has a lengthwise elasticity of from 60% to 250%, e.g., from 80% to 140%. This material may also preferably have a crosswise elasticity of up to 100%, e.g., of from 5% to 30%.

The material of the two bridles 5 and 7 also preferably has a lengthwise elasticity of up to 250%, e.g., from 30% to 100%. This material may preferably have a crosswise elasticity of up to 100%, e.g., of from 5% to 30%.

The material of the elongated tape 1 may comprise a textile strip and/or a neoprene foam. Preferably, the material comprises a spacer fabric.

The material of the two bridles 5 and 7 may comprise a textile strip and/or a neoprene foam. Furthermore, the bridles 5 and 7 may have velcro strips 9, 9' attached at the ends thereof. The bridles 5, 7 of the bandage of the present invention may be individually adjustable.

The bandage may be capable of being changed over from the right ankle joint version or the left ankle joint version to a version for the respective opposite ankle joint by a rotation of the bandage by 180 degrees.

The invention also relates to a method of treating tarsal distortion and chronic instability of an ankle joint. This method comprises the stabilization of the ankle joint with the bandage of the present invention as set forth above.

The bandage for the ankle joint can also have the form of an elongated tape 1, whereby the elongated tape 1 runs around the heel 11, across the lateral side of the ankle joint 6, across the instep 8 in a medial plantar direction and across the sole 14 of the foot 10 in a lateral plantar direction. The first and second transverse edges of the tape 1 are fastened to the tape itself at locations 2. Two bridles 5 and 7 are attached to the elongated tape 1. The first bridle 7 extends from the lateral side on the forefoot and the second bridle 5 extends from the lateral side on the ankle joint 6. The second bridle 5 being circularly closes around the ankle joint 6 and the first bridle 7 is guided on the forefoot across the instep 8 to the ankle joint 6 and then circularly closes around the ankle joint 6.

The elongated elastic tape can result in a closed figure of eight.

The material for the elongated tape preferably offers a lengthwise elasticity of 60% to 250%, in particular 80% to 140%, and a crosswise elasticity of up to 100%, in particular 5% to 30%.

The bridles 5 and 7 can be made of elastic attachable textile strips, but also of neoprene foam for example. In a further advantageous version of the bandage the material of the bridles 5 and 7 offers a lengthwise elasticity of up to 250%, in particular 30% to 100%, and a crosswise elasticity of up to 100%, in particular 5% to 30%.

Enveloping the foot in elastic tape 1 results in a compressive effect. The form of the elastic tape 1, a figure of eight, corresponds to the anatomical circumstances. The circular bridle 5 at the top of the bandage provides for individual adjustment of the compressive effect and thus individual lateral and medial stabilisation of the upper and lower ankle joint 6.

The individually adjustable lateral bridle 7, running from the forefoot and over the instep 8 to the ankle joint 6, reduces the risk of both inversion and eversion trauma by way of lateral and medial stabilisation.

As both bridles 5 and 7 are individually adjustable, it is possible to adjust the level of compression and support accordingly depending on the indication. Despite good stabilisation the bandage provides for the physiological gait pattern.

The bandage can be used for either the right or left foot The bandage should be fitted so that the bridles 5 and 7 are positioned laterally.

The bandage is donned as for a sock 3. The circular strap 5 is then closed first, followed by the lateral strap 7. This means that the bandage is simple to put on for the patient. Thanks to the opening 4 in the heel 11 section there is no problem in placing the bandage securely on the foot 10 in the correct position.

The bridles 5 and 7 of the bandage are provided with Velcro closures 9, 9' but can also be closed with press fasteners etc.

A material that does not irritate the skin is used as the material for the bandage. This means that textile strips can be utilized, but also neoprene foam for example. Spacer fabric, which is highly breathable, can be used to particular benefit.

The invention claimed is:

1. A bandage for an ankle joint comprising an elongated tape, wherein the elongated tape runs around a heel, across a lateral side of the ankle joint, across an instep in a medial plantar direction and across a sole of a foot in a lateral plantar direction, wherein a first and a second transverse edge of the elongated tape are fastened to the tape itself, wherein a first bridle and a second bridle each have one end attached to the elongated tape, one said end of the first bridle being attached to and extending from a lateral side on a forefoot and the second bridle extending from a lateral side on the ankle joint, wherein the second bridle is circularly closed around the ankle joint and has a free end that extends to and is removably attached at the lateral side of the ankle joint and the first bridle is guided on the forefoot across the instep to the ankle joint and is circularly closed around the ankle joint and over the second bridle, wherein the entire width of the free end of the first bridle lies within the width of the free end of the second bridle at the lateral side of the ankle joint, and the first bridle does not have any portion that goes underneath the foot, and wherein the free end of the first bridle extends to and is removably attached to the second bridle at the lateral side of the ankle joint.

2. The bandage of claim 1, wherein a material of the elongated tape has a lengthwise elasticity of from 60% to 250%.

3. The bandage of claim 2, wherein the material has a lengthwise elasticity of from 80% to 140%.

4. The bandage of claim 1, wherein a material of the elongated tape has a crosswise elasticity of up to 100%.

5. The bandage of claim 4, wherein the material has a crosswise elasticity of from 5% to 30%.

6. The bandage of claim 1, wherein a material of the first and second bridles has a lengthwise elasticity of up to 250%.

7. The bandage of claim 6, wherein the material has a lengthwise elasticity of from 30% to 100%.

8. The bandage of claim 1, wherein a material of the first and second bridles has a crosswise elasticity of up to 100%.

9. The bandage of claim 8, wherein the material has a crosswise elasticity of from 5% to 30%.

10. The bandage of claim 2, wherein the material comprises at least one of a textile strip and a neoprene foam.

11. The bandage of claim 5, wherein the material comprises a spacer fabric.

12. The bandage of claim 6, wherein the material comprises at least one of a textile strip and a neoprene foam.

13. The bandage of claim 1, wherein the first and second bridles each have a hook and loop fastening strip attached at the ends thereof.

14. The bandage of claim 1, wherein the first and second bridles are individually adjustable.

15. The bandage of claim 1, wherein the bandage is capable of being changed over from one of a right ankle joint version and a left ankle joint version to a version for an opposite ankle joint by a rotation of the bandage by 180 degrees.

16. A bandage for an ankle joint comprising an elongated tape, wherein the elongated tape runs around a heel, across a lateral side of the ankle joint, across an instep in a medial plantar direction and across a sole of a foot in a lateral plantar direction, wherein a first and a second transverse edge of the elongated tape are fastened to the tape itself to form a sock with a foot opening, a heel opening, and a leg opening, wherein a first bridle and a second bridle each have one end attached to the elongated tape, one said end of the first bridle being attached to and extending from a lateral side on a forefoot and the second bridle extending from a lateral side on the ankle joint, wherein the second bridle is circularly closed around the ankle joint and has a free end that is removably attached to the lateral side of the ankle joint and the first bridle is guided on the forefoot across the instep and has a free end extending to the lateral side of the ankle joint wherein the first bridle is circularly closed around the ankle joint and over the second bridle such that the free end of the first bridle is removably attached to the second bridle on the lateral side of the ankle joint, wherein the entire width of a free end of the first bridle lies within the width of the free end of then second bridle at the lateral side of the ankle joint, and the first bridle does not have any portion that passes underneath the foot, and wherein the material of the elongated tape has a lengthwise elasticity of from 60% to 250% and a crosswise elasticity of up to 100%, and wherein the material of the first and second bridles has a lengthwise elasticity of up to 250% and a crosswise elasticity of up to 100%.

17. The bandage of claim 16, wherein a material of the elongated tape has a lengthwise elasticity of from 80% to 140% and a crosswise elasticity of 5% to 30%.

18. The bandage of claim 16, wherein a material of the first and second bridles has a lengthwise elasticity of 30% to 100% and a crosswise elasticity of 5% to 30%.

19. The bandage of claim 17, wherein the material of the first and second bridles has a lengthwise elasticity of 30% to 100% and a crosswise elasticity of 5% to 30%.

20. A method of treating tarsal distortion and chronic instability of an ankle joint, wherein the method comprises stabilizing the ankle joint with the bandage of claim 1.

21. A method of treating tarsal distortion and chronic instability of an ankle joint, wherein the method comprises stabilizing the ankle joint with the bandage of claim 16.

22. The bandage of claim 1, wherein the free end of the first bridle is removably attached via hook and loop fastening.

23. The bandage of claim 1, wherein the free end of the first bridle has a hook and loop fastening strip that is removably attached.

24. The bandage of claim 1, wherein the free end of the second bridle is removably attached via hook and loop fastening.

25. The bandage of claim 1, wherein the free end of the second bridle has a hook and loop fastening strip that is removably attached.

26. The bandage of claim 1, wherein the first and second transverse edges of the elongated tape are fastened to the tape itself to form a sock with a foot opening, a heel opening, and a leg opening.

27. A bandage for an ankle joint comprising:

a sock member having a foot opening allowing a portion of a foot to pass therethrough, a heel opening configured to expose a heel of the foot, and an ankle joint opening allowing a portion of a leg to pass therethrough;

the sock member extending across a lateral side of the ankle joint, an instep of the foot, and a sole of the foot;

a first strap having an elasticity, one end which is attached to a portion of the sock member which surrounds the ankle joint, and a free end which extends around the portion of the sock member which surrounds the ankle joint;

a second strap having an elasticity and only two ends, one end which attached to a lateral side on a forefoot portion of the sock member, and a free end which extends over the first strap and around the portion of the sock member which surrounds the ankle joint;

the free end of the first strap being connected via a first hook and loop fastening strip on the lateral side of the ankle joint and to the portion of the sock member which surrounds the ankle joint; and the free end of the second strap being connected via a second hook and loop fastening strip on the lateral side of the ankle joint and to the first strap over the ankle joint, wherein the entire width of the free end of the second strap lies within a width of the free end of the first strap at the lateral side of the ankle joint, and the second strap does not have any portion between the one end and the free end of the second strap that goes underneath the foot.

28. A method of treating tarsal distortion and chronic instability of an ankle joint, wherein the method comprises stabilizing the ankle joint with the bandage of claim 27.

29. The bandage of claim 27, wherein the first and second straps each have only two ends and wherein a material of the first and second straps has a lengthwise elasticity of 30% to 100% and a crosswise elasticity of 5% to 30%.

* * * * *